United States Patent [19]

Misra

[11] Patent Number: 4,956,172

[45] Date of Patent: Sep. 11, 1990

[54] AMMONIUM ALUMINUM PHOSPHATE

[75] Inventor: Chanakya Misra, Pittsburgh, Pa.

[73] Assignee: Aluminum Company of America, Pittsburgh, Pa.

[21] Appl. No.: 398,066

[22] Filed: Aug. 24, 1989

Related U.S. Application Data

[63] Continuation-in-part of Ser. No. 143,179, Jan. 13, 1988, abandoned.

[51] Int. Cl.$^5$ .................. A61K 7/22; C01B 25/36; C01B 25/45; C08K 3/32
[52] U.S. Cl. .................. 424/54; 423/306; 423/308; 423/311; 424/57; 523/105; 524/415; 524/584; 524/586
[58] Field of Search .................. 423/306, 308, 311; 424/54, 57; 523/105; 524/415, 584, 586

[56] References Cited

U.S. PATENT DOCUMENTS

| | | | |
|---|---|---|---|
| 3,726,960 | 4/1973 | Bell | 423/306 |
| 4,542,001 | 9/1985 | Iino et al. | 423/308 |
| 3,729,546 | 4/1973 | Bell | 423/386 |

FOREIGN PATENT DOCUMENTS 521223 7/1976 U.S.S.R. .................. 423/306

OTHER PUBLICATIONS

J. J. Pluth et al, "Structure of NH$_4$Al$_2$(OH)(CH$_2$O)(PO$_4$)$_2$.H$_2$O, the Ammonium-Aluminum Analog of GaPO$_4$. 2H$_2$O and Leucophosphite", *Acta Cryst.* (1984). C40, 2008-2011.

John B. Parise, "Preparation and Structure of the Aluminum Ammonium Phosphate Dihydrate Al$_2$(NH$_4$)OH(PO$_4$.2H$_2$O: A Tunnel Structure with Ammonium Ions in the Channels", *Acta Cryst.* (1984), C40, 1641-1643.

*Primary Examiner*—Robert L. Stoll
*Assistant Examiner*—Wayne A. Lange
*Attorney, Agent, or Firm*—Daniel A. Sullivan, Jr.

[57] ABSTRACT

A novel crystalline aluminum ammonium phosphate, characterized by predominantly equiaxed crystals, is provided of the formula: Al$_2$(NH$_4$)OH(PO$_4$)$_2$.2H$_2$O. The phosphate is useful as a dentifrice polishing agent and filler for plastics. The novel product can be prepared by reacting aluminum trihydroxide with diammonium orthophosphate or monobasic ammonium phosphate. By heating at elevated temperature, the product can be converted to the tridymite form of aluminum phosphate.

15 Claims, 1 Drawing Sheet

AMMONIUM ALUMINUM PHOSPHATE

This application is a continuation-in-part of application Ser. No. 07/143,179 filed Jan. 13, 1988, abandoned.

TECHNICAL FIELD

The invention relates to a novel aluminum ammonium phosphate useful, for instance, as a dentifrice polishing agent and as a filler in plastics, to a method for the preparation of said phosphate and to its conversion to crystalline aluminum phosphate in the tridymite form.

BACKGROUND OF INVENTION

A number of aluminum phosphates are known. For example, U.S. Pat. No. 2,909,451 discloses the reaction of a water-soluble aluminum salt and at least a stoichiometric amount of a water-soluble orthophosphate in an aqueous medium to produce a precipitate.

Similarly, U.S. Pat. No. 3,348,910 describes the preparation of magnesium ammonium phosphate by reacting a magnesium compound such as magnesium hydroxide with an excess of monoammonium dihydrogen phosphate.

Complex phosphates are illustrated by U.S. Pat. No. 2,550,490 of the formula:

$$MM'_3H_{14}(PO_4)_8 \cdot 4H_2O$$

where M is an alkali metal including the ammonium radical, and M' is aluminum or iron. The compounds are useful as baking acids.

Lapina et al. in the article, "NATURE OF THE COMPOUNDS FORMED ON NEUTRALIZATION OF PHOSPHORIC ACID CONTAINING ALUMINUM AND IRON BY AMMONIA", *J. Appl. Chem. USSR*, pp 4–7, a translation from Zhurnal Prikladnoi Khimii, Vol. 45, No. 1, pp 6–11, Jan., 1972 (Consultants Bureau, Plenum Publishing, New York), describes an ammonium aluminum phosphate in the form of rhombic platelets having the formula: $NH_4Al_2(PO_4)_2OH \cdot 2.5H_2O$. A tabular presentation of an X-ray diffraction pattern for this material is presented. The article lacks complete information on how this phosphate was made.

DISCLOSURE OF INVENTION

It has now been discovered that a novel crystalline aluminum phosphate can be prepared which is useful as a dentifrice polishing agent and as a filler in plastics. A photo microprint of the crystal structure is shown in FIG. 1. The individual crystals are agglomerated in varying degrees. The novel phosphate of the invention corresponds to the general chemical formula:

which, but for the chemically combined water, is the formula of Lapina et al. mentioned above. As will be observed from FIG. 1, unlike the rhombic platelets of Laspina et al, the crystals of the material of the invention are essentially equiaxed and may be characterized by a diameter to thickness ratio more in the range of about 1 to 2, in contrast to values generally greater than 5 for platelets.

The crystals of the invention will generally have a size between about 1 and about 20 μm and their agglomerates will be correspondingly shifted to higher values in the range of about 2 to about 40 μm.

The aluminum ammonium phosphate of the invention can be prepared by reacting aluminum trihydroxide [Al(OH)$_3$] and an ammonium hydrogen phosphate of the formula:

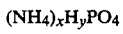

wherein x and y are integers of 1 or 2 providing the total of x and y is 3. The reaction is carried out at elevated temperature.

Quite surprisingly, the crystalline product of the invention can be converted to crystalline aluminum phosphate in the tridymite form, at elevated temperature of at least about 300° C.

MODES FOR CARRYING OUT THE INVENTION

Figure 1:
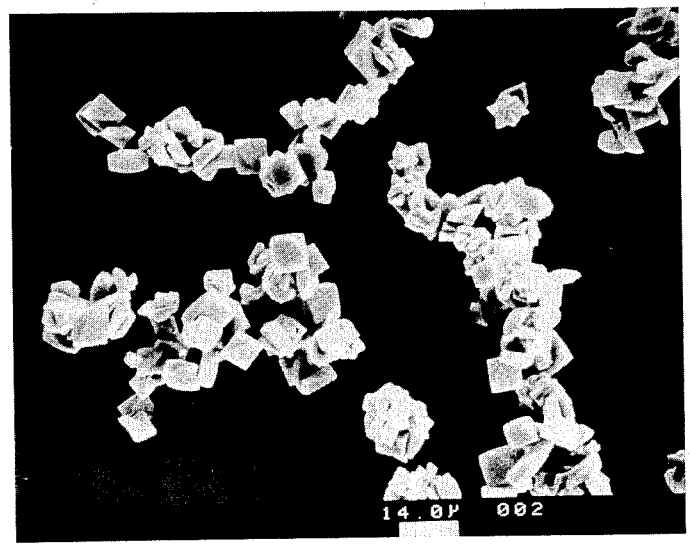
FIG. 1 is a photo microprint (#002) of crystals of the novel phosphate. A scale of 14 microns is shown on the photoprint.

The novel aluminum ammonium phosphate can be prepared by reacting aluminum trihydroxide and diammonium orthophosphate $(NH_4)_2HPO_4$ or monobasic ammonium phosphate $NH_4H_2PO_4$ in a molar ratio of between about 0.5 to about 1.0 moles of aluminum trihydroxide per mole of phosphate. In general, the amount of mono- and/or dibasic ammonium phosphate used is in excess of the stoichiometric requirements for the formation of the aluminum ammonium phosphate of the invention. An aqueous medium is typically employed and the reaction conducted with agitation at above atmospheric pressure. The temperature of the reaction can be between about 125° C. and about 250° C. The product can be washed, dried and is then available as a free flowing crystalline product.

The following examples will serve to illustrate the invention and preferred embodiments. All parts and percentages are by weight unless otherwise indicated.

EXAMPLE 1

Into a one liter stainless steel vessel was placed 30 grams (0.385 mole) aluminum hydroxide, 60 grams (0.52 mole) of ammonium monobasic phosphate and 400 grams of water. The vessel was closed and the mixture agitated and heated at 200° C. over a period of 4 hours. After cooling down to room temperature, the vessel was opened and the product (60 grams) was then filtered, washed and dried, and identified as $Al_2(NH_4)OH(PO_4)_2 \cdot 2H_2O$ composed of nearly uniform crystals in agglomerates of about 20 μm in average size as shown in FIG. 1. The individual crystals of the agglomerates exhibit diameter to thickness ratios predominantly in the range of 1 to 2. A Table showing the X-ray diffraction pattern of the product of Example 1 follows, it appearing to be essentially the same pattern reported by Lapina et al. for their above-mentioned product in the form of rhombic platelets:

| POS: 1 | 22-JUL-87 | 08:05:36 | LSN(ID): 725420 | X-RO: 011269 |
|---|---|---|---|---|
| 2THETA FROM: | 7 | | MAX CTS/SEC: | 6549 |
| 2THETA TO: | 87 | | IC012: | 3778838 |
| STEP PEAK: | .03 | | SENSITIVITY: | 2 |
| STEP-BKGRND: | .09 | | SHOULDER CT: | 10 |

-continued

| 2-THETA | D-SPACE | NET-C/S | I/I-MAX |
|---------|---------|---------|---------|
| 11.69 | 7.5691 | 1114 | 17.6 |
| 13.15 | 6.7324 | 4738 | 74.8 |
| 14.87 | 5.9574 | 6332 | 100.0 |
| 15.34 | 5.7760 | 135 | 2.1 |
| 19.00 | 4.6700 | 2951 | 46.6 |
| 20.68 | 4.2941 | 963 | 15.2 |
| 21.20 | 4.1902 | 1558 | 24.6 |
| 21.88 | 4.0621 | 328 | 5.2 |
| 22.18 | 4.0078 | 102 | 1.6 |
| 23.73 | 3.7487 | 1989 | 31.4 |
| 25.33 | 3.5161 | 481 | 7.6 |
| 26.63 | 3.3470 | 860 | 13.6 |
| 28.09 | 3.1766 | 276 | 4.4 |
| 29.44 | 3.0339 | 2117 | 33.4 |
| 30.12 | 2.9670 | 2942 | 46.5 |
| 31.51 | 2.8392 | 1709 | 27.0 |
| 31.99 | 2.7977 | 2159 | 34.1 |
| 32.53 | 2.7523 | 127 | 2.0 |
| 33.97 | 2.6390 | 2709 | 42.8 |
| 35.56 | 2.5246 | 405 | 6.4 |
| 35.98 | 2.4960 | 300 | 4.7 |
| 36.52 | 2.4602 | 527 | 8.3 |
| 37.53 | 2.3965 | 544 | 8.6 |
| 38.62 | 2.3310 | 1311 | 20.7 |
| 39.58 | 2.2769 | 332 | 5.2 |
| 39.91 | 2.2588 | 343 | 5.4 |
| 40.30 | 2.2379 | 364 | 5.8 |
| 40.48 | 2.2283 | 462 | 7.3 |
| 41.94 | 2.1540 | 438 | 6.9 |
| 42.37 | 2.1332 | 294 | 4.6 |
| 43.01 | 2.1028 | 470 | 7.4 |
| 43.36 | 2.0868 | 190 | 3.0 |
| 43.68 | 2.0720 | 356 | 5.6 |
| 45.86 | 1.9787 | 787 | 12.4 |
| 46.36 | 1.9585 | 205 | 3.2 |
| 46.87 | 1.9383 | 314 | 5.0 |
| 47.37 | 1.9191 | 573 | 9.1 |
| 47.78 | 1.9036 | 511 | 8.1 |
| 48.04 | 1.8939 | 334 | 5.3 |
| 48.19 | 1.8883 | 352 | 5.6 |
| 48.52 | 1.8762 | 621 | 9.8 |
| 48.88 | 1.8634 | 235 | 3.7 |
| 49.13 | 1.8543 | 338 | 5.3 |
| 49.93 | 1.8265 | 95 | 1.5 |
| 51.40 | 1.7777 | 463 | 7.3 |
| 51.67 | 1.7690 | 491 | 7.8 |
| 52.19 | 1.7526 | 98 | 1.6 |
| 52.67 | 1.7379 | 412 | 6.5 |
| 54.71 | 1.6776 | 300 | 4.7 |
| 54.82 | 1.6746 | 284 | 4.5 |
| 55.21 | 1.6637 | 317 | 5.0 |
| 55.96 | 1.6431 | 708 | 11.2 |
| 56.29 | 1.6343 | 324 | 5.1 |
| 57.39 | 1.6060 | 80 | 1.3 |
| 57.73 | 1.5969 | 184 | 2.9 |
| 58.12 | 1.5871 | 268 | 4.2 |
| 58.48 | 1.5782 | 192 | 3.0 |
| 58.75 | 1.5716 | 297 | 4.7 |
| 59.26 | 1.5593 | 197 | 3.1 |
| 60.58 | 1.5285 | 366 | 5.8 |
| 60.79 | 1.5237 | 217 | 3.4 |
| 61.22 | 1.5141 | 297 | 4.7 |
| 61.39 | 1.5102 | 225 | 3.6 |
| 62.92 | 1.4771 | 307 | 4.8 |
| 63.34 | 1.4683 | 161 | 2.5 |
| 63.57 | 1.4635 | 136 | 2.1 |
| 65.51 | 1.4249 | 202 | 3.2 |
| 65.62 | 1.4227 | 157 | 2.5 |
| 65.83 | 1.4187 | 182 | 2.9 |
| 65.92 | 1.4170 | 206 | 3.2 |
| 66.13 | 1.4130 | 127 | 2.0 |
| 67.12 | 1.3946 | 123 | 1.9 |
| 69.71 | 1.3489 | 111 | 1.8 |
| 69.84 | 1.3467 | 101 | 1.6 |
| 70.84 | 1.3301 | 92 | 1.5 |
| 71.08 | 1.3263 | 168 | 2.7 |
| 71.32 | 1.3224 | 89 | 1.4 |
| 72.08 | 1.3103 | 257 | 4.1 |
| 75.31 | 1.2619 | 86 | 1.4 |
| 75.46 | 1.2597 | 106 | 1.7 |
| 77.38 | 1.2332 | 141 | 2.2 |
| 77.57 | 1.2307 | 165 | 2.6 |
| 77.77 | 1.2280 | 138 | 2.2 |

EXAMPLE 2

The procedure of Example 1 is repeated substituting 60 grams of diammonium orthophosphate for the ammonium monobasic phosphate, and similar results are obtained.

EXAMPLE 3

The product of Example 1 was heated at a temperature of 400° C. for 2 hours in an electric oven whereby it was converted to pure crystalline aluminum phosphate in the tridymite form as identified by X-ray diffraction.

The novel aluminum ammonium phosphate of the invention can be employed in dentifrices as the sole polishing agent or in combination with other polishing agents such as dicalcium phosphate in amounts between about 10% and about 60% by weight of the dentifrice.

The novel phosphate can also be employed as a filler in plastics such as polyethylene and polypropylene in amounts of between about 10% and about 60% by weight of the plastic.

While the invention has been illustrated by alternative embodiments, obvious variations may occur to one of ordinary skill and thus the invention is intended to be limited only by the appended claims.

What is claimed is:

1. Essentially equiaxed crystals of aluminum ammonium phosphate of chemical formula $Al_2(NH_4)OH(PO_4)_2$ plus chemically combined water, having an X-ray diffraction pattern essentially as shown in the Table of Example 1.

2. Crystals as claimed in claim 1 having a diameter to thickness ratio in the range of about 1 to 2.

3. A crystalline phosphate as claimed in claim 1 corresponding to the chemical formula: $Al_2(NH_4)OH(PO_4)_2 \cdot 2H_2O$.

4. A phosphate of claim 1 comprising crystals with a size between about 1 and about 20 μm.

5. A phosphate of claim 1 comprising agglomerates of the crystals, the agglomerates having a size between about 2 and about 40 μm.

6. A dentifrice comprising a polishing agent of the phosphate crystals of claim 1.

7. A plastic comprising a filler of the phosphate crystals of claim 1.

8. A process for preparing a novel aluminum ammonium phosphate as claimed in claim 1, comprising reacting aluminum trihydroxide and an ammonium hydrogen phosphate of the formula:

$$(NH_4)_x H_y PO_4$$

wherein x and y are integers of 1 or 2 providing the total of x and y is 3, the reaction occurring at a temperature and pressure effective for producing said novel aluminum ammonium phosphate.

9. The process of claim 8 wherein the reaction temperature is between about 125° C. and about 250° C.

10. The process of claim 8 wherein the ammonium hydrogen phosphate reactant has the formula:

$$NH_4H_2PO_4$$

11. A process for preparing crystalline aluminum phosphate in the tridymite form comprising heating the product of claim 1 for a time and temperature sufficient to effect conversion to crystalline aluminum phosphate in the tridymite form.

12. The process of claim 11 wherein the temperature is at least about 300° C.

13. The process of claim 11 wherein the temperature is at least about 400° C.

14. A process of preparing crystalline aluminum phosphate in the tridymite form comprising reacting aluminum trihydroxide and an ammonium hydrogen phosphate of the formula:

$$(NH_4)_xH_yPO_4$$

wherein x and y are integers of 1 or 2 providing the total of x and y is 3, and then thermally decomposing the resulting ammonium aluminum phosphate compound.

15. The process of claim 11 wherein the temperature of decomposition is above 300° C.

* * * * *

UNITED STATES PATENT AND TRADEMARK OFFICE
CERTIFICATE OF CORRECTION

PATENT NO. : 4,956,172
DATED : September 11, 1990
INVENTOR(S) : Chanakya Misra

It is certified that error appears in the above-identified patent and that said Letters Patent is hereby corrected as shown below:

On the title page, item [56] References Cited: under OTHER PUBLICATIONS

In the Publications    Change "$(CH_2O)$ to --$(H_2O)$--.

In the Publications    Change "$(PO_4\ 2H_2O:$" to --$(PO_4)_2 \cdot 2H_2O$:--.

Col. 2, Line 67    Change "3778838" to --378838--.

Signed and Sealed this

Fifth Day of May, 1992

Attest:

DOUGLAS B. COMER

*Attesting Officer*    *Acting Commissioner of Patents and Trademarks*